US008486879B2

(12) United States Patent
Rumberger et al.

(10) Patent No.: US 8,486,879 B2
(45) Date of Patent: *Jul. 16, 2013

(54) HYPOCHLORITE DENTURE COMPOSITIONS AND METHODS OF USE

(71) Applicant: The Clorox Company, Oakland, CA (US)

(72) Inventors: Evan Rumberger, Pleasanton, CA (US); William L. Smith, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/720,743

(22) Filed: Dec. 19, 2012

(65) Prior Publication Data

US 2013/0109608 A1    May 2, 2013

Related U.S. Application Data

(63) Continuation of application No. 12/903,471, filed on Oct. 13, 2010, now Pat. No. 8,361,942, which is a continuation-in-part of application No. 12/620,932, filed on Nov. 18, 2009, now Pat. No. 8,287,755.

(60) Provisional application No. 61/121,029, filed on Dec. 9, 2008, provisional application No. 61/351,433, filed on Jun. 4, 2010.

(51) Int. Cl.
| | |
|---|---|
| *A61Q 11/02* | (2006.01) |
| *A61Q 11/00* | (2006.01) |
| *A61K 8/20* | (2006.01) |
| *C01B 11/06* | (2006.01) |

(52) U.S. Cl.
USPC ........... 510/116; 510/117; 510/302; 510/298; 510/349; 510/380; 510/446; 252/187.27; 252/187.28; 252/187.29; 252/187.3; 252/186.37; 422/28; 422/29

(58) Field of Classification Search
USPC ............... 252/187.27, 187.28, 187.29, 187.3, 252/186.37; 510/116, 117, 298, 302, 349, 510/380, 446; 422/28, 29
See application file for complete search history.

(56) References Cited

U.S. PATENT DOCUMENTS

| | | | |
|---|---|---|---|
| 1,471,987 A | 10/1923 | Vogt | |
| 1,481,003 A | 1/1924 | Gegenheimer | |
| 1,961,576 A | 6/1934 | Taylor | |
| 2,409,718 A | 11/1941 | Snell et al. | |
| 2,320,279 A | 5/1943 | Kalusdian | |
| 2,498,344 A | 2/1950 | Rider et al. | |
| 2,921,911 A | 1/1960 | Staubly et al. | |
| 3,113,111 A | 12/1963 | Myerson | |
| 3,257,450 A | 6/1966 | Globus | |
| 3,337,466 A | 8/1967 | Puetzer et al. | |
| 3,342,674 A | 9/1967 | Kowalski | |
| 3,446,893 A * | 5/1969 | Hanford et al. | 424/76.3 |
| 3,640,879 A | 2/1972 | Fitzgerald, Jr. | |
| 3,755,179 A | 8/1973 | Fitzgerald, Jr. | |
| 3,769,224 A | 10/1973 | Inamorato | |
| 3,793,211 A | 2/1974 | Kohlhepp et al. | |
| 3,821,117 A | 6/1974 | Breece et al. | |
| 3,936,385 A | 2/1976 | Cheng | |
| 4,035,484 A | 7/1977 | Faust et al. | |
| RE29,473 E | 11/1977 | Fitzgerald, Jr. | |
| 4,082,841 A | 4/1978 | Pader | |
| 4,087,360 A * | 5/1978 | Faust et al. | 210/701 |
| 4,146,676 A | 3/1979 | Saeman et al. | |
| 4,256,599 A | 3/1981 | Krisp et al. | |
| 4,276,349 A | 6/1981 | Saeman | |
| 4,362,639 A | 12/1982 | Eoga | |
| 4,421,664 A | 12/1983 | Anderson et al. | |
| 4,552,679 A | 11/1985 | Schobel et al. | |
| 4,657,784 A | 4/1987 | Olson | |
| 4,671,972 A | 6/1987 | Schobel et al. | |
| 4,692,335 A | 9/1987 | Iwanski | |
| 4,707,160 A | 11/1987 | Chun et al. | |
| 4,731,195 A | 3/1988 | Olson | |
| 4,933,102 A | 6/1990 | Olson | |

(Continued)

FOREIGN PATENT DOCUMENTS

| | | |
|---|---|---|
| GB | 490384 | 8/1938 |
| GB | 550020 | 12/1942 |

(Continued)

OTHER PUBLICATIONS

International Search Report of PCT Application No. PCT/US2009/065090, Jan. 21, 2010, 3 pgs.
International Search Report of PCT Application No. PCT/US2010/052602, Dec. 9, 2010, 3 pgs.
International Search Report of PCT Application No. PCT/US2010/52487, Jan. 4, 2011, 3 pgs.
International Search Report of PCT Application No. PCT/US2010/56117, Jan. 14, 2011, 3 pgs.
International Search Report of PCT Application No. PCT/US2010/56139, Jan. 18, 2011, 3 pgs.

*Primary Examiner* — Joseph D Anthony
(74) *Attorney, Agent, or Firm* — Alok Goel; Stacy Hegle Combs

(57) ABSTRACT

A solid composition including calcium and/or magnesium hypochlorite, a builder (e.g., one or more of carbonate, bicarbonate, sesquicarbonate), an acid, a water-soluble polymer, at least one anionic surfactant, and optionally, a hydrotrope. The composition does not include any potassium hypochlorite, sodium hypochlorite, lithium hypochlorite, N-halogenated compounds, peroxides, persulfates, hydantoins, isocyanurates, or carboxylic acids that also have hydroxyl, amino, amido, imino, or imido groups. Upon dissolution of the composition in water, the calcium and/or magnesium hypochlorite and acid react to form hypochlorous acid. The use of hypochlorous acid, rather than direct use of an alkaline or alkaline earth hypochlorite results in a composition that is typically acidic rather than basic, and that results in improved cleaning. The composition is particularly suited for cleaning and disinfecting dentures.

16 Claims, No Drawings

U.S. PATENT DOCUMENTS

| | | | |
|---|---|---|---|
| 4,961,872 A | 10/1990 | Sinclair | |
| 5,114,647 A | 5/1992 | Levesque et al. | |
| 5,133,892 A | 7/1992 | Chun et al. | |
| 5,407,598 A * | 4/1995 | Olson et al. | 252/186.35 |
| 5,534,178 A | 7/1996 | Bailly et al. | |
| 5,599,781 A | 2/1997 | Haeggberg et al. | |
| 5,753,602 A | 5/1998 | Hung et al. | |
| 5,869,438 A | 2/1999 | Svendsen et al. | |
| 5,981,457 A | 11/1999 | Ahmed | |
| 6,071,539 A | 6/2000 | Robinson et al. | |
| 6,146,538 A * | 11/2000 | Martin | 210/698 |
| 6,211,129 B1 | 4/2001 | Gladfelter et al. | |
| 6,298,871 B1 | 10/2001 | Pickens et al. | |
| 6,358,909 B1 | 3/2002 | Ochomogo | |
| 6,426,111 B1 * | 7/2002 | Hirsch | 426/590 |
| 6,468,950 B1 | 10/2002 | Kawasaki et al. | |
| 6,589,443 B1 * | 7/2003 | Olson et al. | 252/186.2 |
| 6,852,238 B2 | 2/2005 | Connelly, Jr. | |
| 6,863,830 B1 | 3/2005 | Purdy et al. | |
| 6,969,527 B2 | 11/2005 | Brennan et al. | |
| 6,995,129 B2 | 2/2006 | Olson et al. | |
| 7,309,444 B2 | 12/2007 | Connelly, Jr. | |
| 7,410,938 B2 | 8/2008 | Brennan | |
| 7,517,413 B2 | 4/2009 | van Buskirk et al. | |
| 2002/0189634 A1 | 12/2002 | Vanhauwermeiren et al. | |
| 2002/0198128 A1 | 12/2002 | Perkins et al. | |
| 2003/0086878 A1 | 5/2003 | Rajaiah et al. | |
| 2004/0081690 A1 * | 4/2004 | Gauthier et al. | 424/465 |
| 2004/0082491 A1 * | 4/2004 | Olson et al. | 510/375 |
| 2004/0266650 A1 | 12/2004 | Lambotte et al. | |
| 2005/0143274 A1 | 6/2005 | Ghosh et al. | |
| 2005/0233900 A1 | 10/2005 | Smith et al. | |
| 2005/0288209 A1 | 12/2005 | Fletcher | |
| 2006/0258553 A1 | 11/2006 | Catalfamo et al. | |
| 2008/0083071 A1 * | 4/2008 | Tremblay et al. | 8/109 |
| 2008/0166176 A1 | 7/2008 | Rees et al. | |
| 2009/0042756 A1 | 2/2009 | Muzik et al. | |
| 2009/0148342 A1 | 6/2009 | Bromberg et al. | |
| 2009/0165818 A1 | 7/2009 | Smith et al. | |
| 2010/0140544 A1 | 6/2010 | Smith et al. | |

FOREIGN PATENT DOCUMENTS

| | | |
|---|---|---|
| GB | 552803 | 4/1943 |
| GB | 606431 | 8/1948 |
| GB | 739046 | 10/1955 |
| WO | WO 01/36115 | 5/2001 |
| WO | WO 2010/077468 | 7/2010 |

* cited by examiner

HYPOCHLORITE DENTURE COMPOSITIONS AND METHODS OF USE

CROSS-REFERENCE TO RELATED APPLICATIONS

The present application is a continuation of U.S. patent application Ser. No. 12/903,471, filed Oct. 13, 2010, now U.S. Pat. No. 8,361,942, which is a continuation in part of U.S. patent application Ser. No. 12/620,932, filed Nov. 18, 2009, now U.S. Pat. No. 8,287,755, which claims the benefit of provisional U.S. Patent Application Ser. No. 61/121,029, filed Dec. 9, 2008. U.S. patent application Ser. No. 12/903, 471 also claims the benefit of provisional U.S. Patent Application Ser. No. 61/351,433, filed Jun. 4, 2010. Each of the above patent matters are hereby incorporated by reference in their entirety.

BACKGROUND OF THE INVENTION

1. The Field of the Invention

The present invention relates generally to solid single-layered cleaning compositions. These compositions may be used to clean and disinfect dentures, other dental appliances, or cleaning other oral surfaces (e.g., as a mouthwash, endodontic root canal disinfection).

2. Background and Relevant Art

Solid bleach compositions have progressed for decades and created a large chemical industry devoted to cleaning and disinfecting hard and soft surfaces. N-chloro hydantoins, N-chloro isocyanurates, sodium hypochlorite, and calcium hypochlorite are used quite frequently in bleach compositions for many companies because they are cheap to produce and they are highly effective. However, these bleach compositions have several disadvantages that limit their usefulness. Sodium hypochlorite is only available as a liquid at room temperature. Calcium hypochlorite leaves residue. Chlorinated hydantoins and isocyanurates lack long term solution stability and generate malodor. All these disadvantages present compositions which consumers may not prefer.

BRIEF SUMMARY OF THE INVENTION

The presently claimed invention solves some of these problems in the art with compositions and methods related to denture cleaning compounds comprising hypochlorite in a single-layered composition. It is contemplated that the composition may also be useful in other oral care environments, such as a mouthwash and as an endodontic root canal disinfectant. Use of calcium and/or magnesium hypochlorite in a single-layered composition (e.g., in tablet form) as taught herein minimizes and/or eliminates the formation of residues that are associated with other calcium hypochlorite compositions. In addition, the compositions do not generate malodors typically associated with the use of chlorinated isocyanurates. The present invention also releases bleach faster than the typical use of halogenated hydantoins. The present invention also dissolves faster than typical commercial products based on calcium hypochlorite or halogenated hydantoins.

One embodiment of the present invention comprises a solid single-layered composition including: a) a hypochlorite selected item the group consisting of calcium hypochlorite, magnesium hypochlorite and mixtures thereof; b) a builder selected from the group consisting of carbonate, bicarbonate, sesquicarbonate and mixtures thereof; c) an acid selected from the group consisting of carboxylic acid, dicarboxylic acid, sulfonic acid, acid sulfate, acid phosphate, and mixtures thereof; d) a water-soluble polymer selected from the group consisting of a polycarboxylate, sulfonated carboxylate, polysulfonate, polyvinylpyrrolidone, polypyridinium salt, polyquaternary ammonium salt, and mixtures thereof; e) at least one anionic surfactant; f) at least one hydrotrope; g) wherein the composition does not contain potassium, hypochlorite, sodium hypochlorite, lithium hypochlorite, N-halogenated compounds, peroxides, persulfates, hydantoins, isocyanurates, carboxylic acids that also have one or more hydroxyl, amino, amido, imino, or imido group moieties; h) and wherein the composition contains only one layer.

Another embodiment of the present invention comprises a solid-layered one-layered composition consisting essentially of a) a hypochlorite selected from the group consisting of calcium hypochlorite, magnesium hypochlorite and mixtures thereof; b) a builder selected from the group consisting of carbonate, bicarbonate, sesquicarbonate and mixtures thereof; c) an acid selected from the group consisting of carboxylic acid dicarboxylic acid, sulfonic acid, an acid sulfate, an acid phosphate, and mixtures thereof; d) a water-soluble polymer selected from the group consisting of a polycarboxylate, a sulfonated carboxylate, a polysulfonate, a polyvinylpyrrolidone, a polypyridinium salt, a polyquaternary ammonium salt, and mixtures thereof; e) at least one anionic surfactant; f) at least one hydrotrope; g) optionally, a cobuilder selected from the group consisting of a hydroxide, an oxide, a silicate, a phosphate, a borate, and mixtures thereof; h) optionally, colorants, perfumes, sequestrants, anti-corrosion agents, lubricants, binders, fillers, disintegration aids, preservatives, desiccants, and mixtures thereof.

Another embodiment of the present indention is directed to a solid one-layered composition consisting of: a) a hypochlorite selected from the group consisting of calcium hypochlorite, magnesium hypochlorite and mixtures thereof; b) a builder selected from the group consisting of carbonate, bicarbonate, sesquicarbonate and mixtures thereof; c) an acid selected from the group consisting of a carboxylic acid, a dicarboxylic acid, a sulfonic acid, an acid sulfate, an acid phosphate, and mixtures thereof; d) a water-soluble polymer selected from the group consisting of a polycarboxylate, sulfonated carboxylate, polysulfonate, polyvinylpyrrolidone, polypyridinium salt, polyquaternary ammonium, salt, and mixtures thereof; e) at least one anionic surfactant; f) optionally, at least one hydrotrope; g) optionally, a cobuilder selected from the group consisting of a hydroxide, an oxide, a silicate, a phosphate, a borate, and mixtures thereof; h) optionally, colorants, perfumes, sequestrants, anti-corrosion agents, lubricants, binders, fillers, disintegration aids, preservatives, desiccants, and mixtures thereof.

Because the composition includes calcium and/or magnesium hypochlorite and an acid, hypochlorous acid is formed upon dissolution of the composition in water. As such, the composition derives its disinfection and cleaning properties from the hypochlorous acid formed in situ, rather than the hypochlorite alone. The use of hypochlorous acid, rather than direct use of an alkaline or alkaline earth hypochlorite (e.g., calcium hypochlorite) results in a composition that is acidic rather than basic, and which provides improved efficacy.

Further features and advantages of the present invention will become apparent to those of ordinary skill in the art in view of the detailed description of preferred embodiments below, when considered together with the attached claims.

DETAILED DESCRIPTION OF THE PREFERRED EMBODIMENTS

I. Definitions

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage (%) are in weight percent (based on 100% active) of the composition alone, not accounting for any substrate weight. Each of the noted composition components and substrates is discussed in detail below. Additionally, the invention also covers method steps of utilizing the compositions described in the present application.

The term, "comprising", which is synonymous with "including," "containing," or "characterized by," is inclusive or open-ended and does not exclude additional, unrecited elements or method steps. See MPEP 2111.03. See, e.g., Mars Inc. v, H. J. Heinz Co., 377 F.3d 1369, 1376, 71 USPQ2d 1837, 1843 (Fed. Cir. 2004) ("like the term 'comprising,' the terms 'containing' and 'mixture' are open-ended."). Invitrogen Corp. v, Biocrest Mfg., L. P., 327 F.3d 1364, 1368, 66 USPQ2d 1631, 1634 (Fed. Cir. 2003) ("The transition 'comprising' in a method claim indicates that the claim is open-ended and allows for additional steps."); Genentech, Inc. v. Chiron Corp., 112 F.3d 495, 501, 42 USPQ2d 1608, 1613 (Fed. Cir. 1997) See MPEP 2111.03. ("Comprising" is a term of art used in claim language which means that the named elements are essential, but other elements may be added and still form a construct within the scope of the claim); Moleculon Research Corp. v. CBS, Inc., 793 F.2d 1261, 229 USPQ 805 (Fed. Cir. 1986); In re Baxter, 656 F.2d 679, 686, 210 USPQ 795, 803 (CCPA 1981); Ex parte Davis, 80 USPQ 448, 450 (Bd. App. 1948). See MPEP 2111.03.

The term "consisting essentially of" as used herein, limits the scope of a claim to the specified materials or steps "and those that do not materially affect the basic and novel characteristic(s)" of the claimed invention. In re Herz, 537 F.2d 549, 551-52, 190 USPQ 461, 463 (CCPA 1976). See MPEP 2111.03.

The term, "consisting of" as used herein, excludes any element, step, or ingredient not specified in the claim. In re Gray 53 F.2d 520, 11 USPQ 255 (CCPA 1931); Ex Parte Davis, 80 USPQ 448, 450 (Bd. App. 1948). See MPEP 2111.03.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic, cationic, zwitterionic and/or amphoteric agents.

II. Introduction

The present invention is directed to a solid single-layered composition. The solid single-layered composition comprises calcium, hypochlorite, magnesium hypochlorite or mixtures thereof, an acid, a water-soluble polymer, and an anionic surfactant. Optional ingredients may be added to the composition to enhance the efficacy of the solid single-layered composition. Upon dissolution of the composition in water, the calcium and/or magnesium, hypochlorite and acid react to form hypochlorous acid. The composition may be particularly suitable for use in disinfecting dentures or other dental appliances, although it is contemplated that the composition may also be useful in other oral care environments, such as a mouthwash and as an endodontic root canal disinfectant.

The use of hypochlorous acid, rather than direct use of an alkaline or alkaline earth hypochlorite (e.g., calcium hypochlorite) results in a composition that is typically acidic rather than basic. This lower pH speeds the rate of antimicrobial activity, improves the removal of plaque and biofilms including their conditioning layer, and increases the removal of stains from food, beverages and tobacco. Complete removal of biofilms including their conditioning layer increases the incubation time required for bacteria to reattach to the denture to reform a biofilm when subsequently re-exposed to bacteria. Furthermore, the lower pH also increases the removal of dental calculus and other hard to remove calcium deposits. This is because the solubility of the calcium is significantly greater within the acidic environment.

Since hypochlorous acid is more effective than hypochlorite ion, a lower concentration of hypochlorous acid may be used. This largely eliminates the formation of unpleasant odors from the reaction of hypochlorite ion and proteins. In addition, the hypochlorous acid works more quickly so that shorter contact times with the cleaning solution produce the desired results. Hypochlorous acid solutions by virtue of their lower effective concentration and their lower pH are also less corrosive to some materials used to construct dentures and dental appliances.

Although the pH of the mixed and prepared composition may be as high as about 9, preferably, the pH of the hypochlorous acid disinfecting composition is between about 5 and about 8. In another embodiment, the pH of the hypochlorous acid disinfecting composition is between about 6 and about 7. In one embodiment, the pH is preferably acidic (i.e., less than 7), most preferably between about 5.5 and about 6.5.

Generally, the concentration of hypochlorous acid will be selected to remove stains, biofilms and kill or remove at least 99.9% of bacteria, viruses, and fungi. The concentration will depend on the use instructions for the product. For example, a product designed for soaking dentures overnight would contain at least 10 ppm, preferably more than about 20 ppm, more preferably more than about 30 ppm, and most preferably more than about 20 ppm of hypochlorous acid. A product designed to work in 3 to 5 minutes would contain at least 50 ppm, preferably more than about 100 ppm, more preferably more than about 150 ppm, and most preferably more than about 300 ppm of hypochlorous acid, in order to minimize the potential to form unpleasant odors or damage surfaces if spilled the maximum concentration is about 1500 ppm, preferably less than about 1000 ppm, more preferably less than about 600 ppm, and most preferably less than about 400 ppm of hypochlorous acid.

III. Oxidants

The solid single-layered composition contains calcium hypochlorite, magnesium hypochlorite or mixtures thereof. These hypochlorite salts include anhydrous varieties as well as the various hydrates, double salts such as monobasic and dibasic forms, and triple salts. The hypochlorite salts may be crystalline or amorphous. The solid single-layered composition does not contain any other types of hypochlorite such as sodium hypochlorite, lithium, hypochlorite, or potassium hypochlorite. Therefore, the composition does not contain any N-halogenated compounds, peroxides, persulfates, hydantoins, isocyanurates, or carboxylic acids that also have hydroxyl, amino, amide, imino, or imido groups. More specific examples of such excluded components include hypobromites, hypoiodites, chlorinated trisodium phosphate dodecahydrates, potassium and sodium dichloroisocyanurates, trichlorocyanuric acid, N-chloroimides, N-chloroamides, N-chlorosulfamide, N-chloroamines, chlorohydantoins such as dichlorodimethyl hydantoin, chlorobromo dimethylhydantoin, and bromo-compounds corresponding to the chloro-compounds above.

The compositions of the present invention do not require a bleach activator. By "bleach activator", it is meant herein a compound which reacts with peroxygen bleach like hydrogen peroxide to form a peracid. The peracid thus formed constitutes the activated bleach. Bleach activators that are not to be used in the composition include, but are not limited to, those belonging to the class of esters, amides, imides, or anhydrides. Examples of bleach activators that are not to be used in the composition include, but are not limited to, TAED, sodium 3,5,5 trimethyl hexanoyloxy-benzene sulphonate, diperoxy dodecanoic acid, nonylamide of peroxyadipic acid, nonylamide of peroxyadipic acid, n-nonanoyloxybenzenesulphonate (NOBS), acetyl triethyl citrate (ATC), n-alkyl alkyl ammonium acetonitrile activators. Additional examples of bleach activators that are not to be used in the composition include, but are not limited to, are N-acyl caprolactams selected from the group consisting of substituted or unsubstituted benzoyl caprolactam, octanoyl caprolactam, nonanoyl caprolactam, hexanoyl caprolactam, decanoyl caprolactam, undecenoyl caprolactam, formyl caprolactam, acetyl caprolactam, propanoyl caprolactam, butanoyl caprolactam pentanoyl caprolactam or mixtures thereof.

In one embodiment, the calcium hypochlorite, magnesium hypochlorite or mixture thereof is present in the composition in an amount of less than about 50%. For example, the calcium and/or magnesium hypochlorite may be present in the composition in an amount ranging from about 0.1% to about 50%, about 0.1% to about 45%, about 0.1% to about 40%, about 0.1% to about 30%, about 0.1% to about 25%, about 0.1% to about 20%, about 0.1% to about 15%, about 0.1% to about 10%, about 0.1% to about 5%, about 5% to about 20%, about 5% to about 15%, about 10% to about 20%, about 10% to about 15% or about 15% to about 20%.

IV. Builders

The composition may contain a builder. The builder may be present in the cleaning composition in an amount ranging from about 10% to about 90%, about 20% to about 90%, about 20% to about 80%, about 20% to about 60%, about 20% to about 50%, about 30% to about 60%, about 35 to about 55%, about 40 to about 50%, about 20% to about 30%, about 30% to about 50%, about 30% to about 45%, about 30% to about 40%, about 20% to about 60%, about 25% to about 60%, about 20% to about 40%, or about 20% to about 30%. The builder can be selected from inorganic builders, such as carbonate, bicarbonate, sesquicarbonate, and mixtures thereof. More specifically, the builder may comprise a carbonate, bicarbonate, or sesquicarbonate of one or more alkali metals. The builder may be in its anhydrous form or any of its stable hydrates, and they may be crystalline or amorphous.

Inclusion of a builder is advantageous, as it can increase the effectiveness of the surfactant. The builder can also function as a softener, a sequestering agent, a buffering agent, or a pH adjusting agent in the cleaning composition. A variety of builders or buffers can be used and they include, but are not limited to, phosphate-silicate compounds, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates, polyhydroxy-sulfonates, and starch derivatives. Builders, when used, include, but are not limited to, organic acids, mineral acids, alkali metal and alkaline earth salts of silicate, metasilicate, polysilicate, borate, sulfates, hydroxide, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2-methylpropanol. Other suitable buffers include ammonium carbamate and acetic acid. Mixtures of any of the above may also be acceptable. Useful inorganic buffers/alkalinity sources include ammonia, the alkali metal carbonates and alkali metal phosphates, e.g., sodium carbonate, sodium polyphosphate. For additional buffers see WO 95/07971, which is incorporated herein by reference. Other preferred pH adjusting agents include sodium or potassium hydroxide. The term silicate is meant to encompass silicate, metasilicate, polysilicate, aluminosilicate and similar compounds. Preferred builders/buffers of the solid single-layered composition include carbonate, bicarbonate, sesquicarbonate and mixtures thereof.

V. Water-Soluble Polymers

The composition may contain a water-soluble polymer. Examples of water-soluble polymers include, but are not limited to, polycarboxylate, sulfonated carboxylate, polysulfonate, polyvinylpyrrolidone ("PVP") a polypyridinium salt, a polyquaternary ammonium salt, and mixtures thereof.

Examples of polycarboxylates include, but are not limited to polymers with sufficient carboxylate ions to achieve water solubility. Carboxylate ions may be derived from various monomers including acrylic acid, methacrylic acid, maleic acid and maleic anhydride. Copolymers of different carboxylate-containing monomers are also suitable as well as copolymers with non carboxylate containing monomers such as methacrylate, acrylonitrile, styrene, ethylene, propylene, and many others. Mixtures of carboxylate containing polymers can also be used.

In one embodiment the molecular weight of the water-soluble polymer may be between about 1,000 to about 10,000 daltons, about 1,000 to about 8,000 daltons, about 1,000 to about 6,000 daltons, about 1,000 to about 5,000 daltons, about 1,000 to about 4,000 daltons, about 1,000 to about 2,000 daltons, about 2,000 to about 10,000 daltons, about 2,000 to about 8,000 daltons, about 2,000 to about 6,000 daltons, about 2,000 to about 5,000 daltons, about 2,000 to about 4,000 daltons, about 3,000 to about 10,000 daltons, about 3,000 to about 8,000 daltons, about 3,000 to about 6,000 daltons, about 3,000 to about 5,000 daltons, about 3,000 to about 4,000 daltons, about 4,000 to about 10,000 daltons, about 4,000 to about 8,000 daltons, about 4,000 to about 6,000 daltons, about 5,000 to about 10,000 daltons, about 5,000 to about 7,500 daltons, or about 7,500 to about 10,000 daltons.

The water-soluble polymer may be present in an amount ranging from about 0.1% to about 60%, about 0.1% to about 50%, about 0.1% to about 40%, about 0.1% to about 30%, about 0.1% to about 20%, about 0.1% to about 15%, about 0.1% to about 10%, about 1% to about 10%, about 1% to about 5%, about 1% to about 3%, about 5% to about 60%, about 5% to about 50%, about 5% to about 40%, about 5% to about 30%, about 5% to about 20%, about 5% to about 10%, about 10% to about 60%, about 10% to about 50%, about 10% to about 40%, about 10% to about 30%, about 10% to about 20%, about 20% to about 60%, about 20% to about 50%, about 20% to about 40%, about 20% to about 30%, about 30% to about 60%, about 30% to about 50%, about 30% to about 40%, or about 40% to about 60%.

VI. Acids

The composition may contain an acid. Examples of acids that can be used with the present invention include, but are not limited to, carboxylic acid, dicarboxylic acid, sulfonic acid, an acid sulfate, an acid phosphate, and mixtures thereof. Specific examples of acids include, but are not limited to, succinic acid, glutaric acid, 3-pyridine sulfonic acid, dodecyl benzene sulfonic acid, and mixtures thereof.

Notably, the composition does not contain carboxylic acids that have one or more hydroxyl, amino, amido, imino, or imido group moieties. Examples of acids that are not to be used in the composition include, but are not limited to citric acid, tartaric acid, and alanine.

The acid may be present in an amount of at least 30%, and in one embodiment at least 50%, of the composition. For example, the acid may be present in an amount ranging from about 30% to about 80%, about 30% to about 70%, about 30% to about 60%, about 30% to about 50%, or about 40% to about 80%, about 40% to about 70%, about 40% to about 60%, about 40% to about 50%, about 50% to about 80%, about 50% to about 70%, or about 50% to about 60%.

In one embodiment, the acid is present in an amount of at least about 50% (e.g., about 50% to about 60%), and the calcium and/or magnesium hypochlorite is present in an amount of about 0.1% to about 5%. This results in the desired relatively low, but effective, concentration of hypochlorous acid upon dissolution of the composition in water.

VII. Cross-Linked Water-Swellable Polymers

The composition may optionally contain a cross-linked water-swellable polymer. Examples of water-swellable polymers include, but are not limited to, cross-linked polycarboxylate, cross-linked sulfonated carboxylate, cross-linked polysulfonate, cross-linked PVP, cross-linked polypyridinium salt, cross-linked polyquaternary ammonium salt, cellulose, cross-linked carboxymethylcellulose, sodium carboxymethylcellulose, and mixtures thereof.

The molecular weight of the water-swellable able polymer may be between about 1,000 to about 10,000 daltons, about 1,000 to about 8,000 daltons, about 1,000 to about 6,000 daltons, about 1,000 to about 5,000 daltons, about 1,000 to about 4,000 daltons, about 1,000 to about 2,000 daltons, about 2,000 to about 10,000 daltons, about 2,000 to about 8,000 daltons, about 2,000 to about 6,000 daltons, about 2,000 to about 5,000 daltons, about 2,000 to about 4,000 daltons, about 3,000 to about 10,000 daltons, about 3,000 to about 8,000 daltons, about 3,000 to about 6,000 daltons, about 3,000 to about 5,000 daltons, about 3,000 to about 4,000 daltons, about 4,000 to about 10,000 daltons, about 4,000 to about 8,000 daltons, about 4,000 to about 6,000 daltons, about 5,000 to about 10,000 daltons, about 5,000 to about 7,500 daltons, and about 7,500 to about 10,000 daltons.

The water-swellable polymer may optionally be present in an amount ranging from about 0.1% to about 60%, about 0.1% to about 50%, about 0.1% to about 40%, about 0.1% to about 30%, about 0.1% to about 20%, about 0.1% to about 15%, about 0.1% to about 10%, about 0.5% to about 10%, about 0.5% to about 5%, about 0.5% to about 3%, about 5% to about 60%, about 5% to about 50%, about 5% to about 40%, about 5% to about 30%, about 5% to about 20%, about 5% to about 10%, about 10% to about 60%, about 10% to about 50%, about 10% to about 40%, about 10% to about 30%, about 10% to 20%, about 20% to about 60%, about 20% to about 50%, about 20% to about 40%, about 20% to about 30%, about 30% to about 60%, about 30% to about 50%, about 30% to about 40%, about 40% to about 60%.

VIII. Surfactants

The composition may contain one or more anionic surfactants. One or more additional surfactants selected from nonionic, cationic, ampholytic, amphoteric and zwitterionic surfactants and mixtures thereof may be included. In some embodiments, although in one embodiment no nonionic surfactants are included. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. Each of the above patents is hereby incorporated by reference. The surfactants may be present at a level of from about 0.1% to about 25%, from about 0.1% to about 20%, from about 0.1% to about 15%, from about 0.1% to shout 10%, from about 0.1% to about 5%, from about 5% to about 20%, from about 5% to about 15%, from about 5% to about 10%, from about 10% to about 20%, from about 10% to about 15%, or from about 15% to about 20%.

The composition comprises an anionic surfactant. Essentially any anionic surfactants useful for detersive purposes can be used in the cleaning composition. These can include salts (including, for example, sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyldiphenyloxide disulfonate, as described herein.

Other anionic surfactants include the isethionates such as the acyl isethionates, N-acyl taurates, fatty acid amides of methyl tauride, alkyl succinates and sulfosuccinates, monoesters of sulfosuccinate (for instance, saturated and unsaturated $C_{12}$-$C_{18}$ monoesters) diesters of sulfosuccinate (for instance saturated and unsaturated $C_6$-$C_{14}$ diesters), and N-acyl sarcosinates. Resin acids and hydrogenated resin acids are may also be suitable, such as rosin, hydrogenated rosin, and resin acids and hydrogenated resin acids present in or derived from tallow oil, although in one embodiment, no resins are included. Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the $C_5$-$C_{17}$acyl-N—($C_1$-$C_4$ alkyl) and —N—($C_1$-$C_2$ hydroxyalkyl) glucamine sulfates, and sulfates of alkylpolysacchanides such as the sulfates of alkylpolyglucoside (the nonionic nonsulfated compounds being described herein). Alkyl sulfate surfactants may be selected from the linear and branched primary $C_{10}$-$C_{18}$ alkyl sulfates, the $C_{11}$-$C_{15}$ branched chain alkyl sulfates, or the $C_{12}$-$C_{14}$ linear chain alkyl sulfates.

Alkyl ethoxysulfate surfactants may be selected from the group consisting of the $C_{10}$-$C_{18}$ alkyl sulfates, which have been ethoxylated with from 0.5 to 20 moles of ethylene oxide per molecule. The alkyl ethoxysulfate surfactant may be a $C_{11}$-$C_{18}$, or a $C_{11}$-$C_{15}$ alkyl sulfate which has been ethoxylated with from 0.5 to 7, or from 1 to 5, moles of ethylene oxide per molecule. One aspect of the invention employs mixtures of the alkyl sulfate and/or sulfonate and alkyl ethoxysulfate surfactants. Such mixtures have been disclosed in PCT Patent Application No. WO 93/18124, herein incorporated by reference.

Anionic sulfonate surfactants suitable for use herein include the salts of $C_5$-$C_{20}$ linear alkylbenzene sulfonates, alkyl ester sulfonates, $C_6$-$C_{22}$ primary or secondary alkane sulfonates, $C_6$-$C_{24}$ olefin sulfonates, sulfonated polycarboxylic acids, alkyl glycerol sulfonates, fatty acyl glycerol sulfonates, fatty oleyl glycerol sulfonates, and any mixtures thereof. Suitable anionic carboxylate surfactants include the alkyl ethoxy carboxylates, the alkyl polyethoxy polycarboxylate surfactants and the soaps (alkyl carboxyls), especially certain secondary soaps as described herein. Suitable alkyl ethoxy carboxylates include those with the formula:

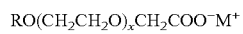

wherein R is a $C_6$ to $C_{18}$ alkyl group, x ranges from 0 to 10, and the ethoxylate distribution is such that, on a weight basis, the amount of material where x is 0 is less than 20% and M is a cation. Suitable alkyl polyethoxypolycarboxylate surfactants include those having the formula RO—(CHR$^1$—CHR$^2$—O)$_x$R$^3$ wherein R is a $C_6$ to $C_{18}$ alkyl group, x is from 1 to 25, R$^1$ and R$^2$ are selected from the group consisting of hydrogen, methyl acid radical, succinic acid radical, hydroxysuccinic acid radical, and mixtures thereof, and R$^3$ is selected from the group consisting of hydrogen, substituted or unsubstituted hydrocarbon having between 1 and 8 carbon atoms, and mixtures thereof.

Suitable soap surfactants include the secondary soap surfactants, which contain a carboxyl unit connected to a secondary carbon. Suitable secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressors.

Other suitable anionic surfactants are the alkali metal sarcosinates of formula R—COM(R$^1$)CH—)COOM, wherein it is a $C_5$-$C_{17}$ linear or branched alkyl or alkenyl group, R$^1$ is a $C_1$-$C_4$ alkyl group and M is an alkali metal ion. Examples are the myristyl and oleoyl methyl sarcosinates in the form of their sodium salts.

Other suitable surfactants include fatty acid sarcosinates which are mild, biodegradable anionic surfactants derived from fatty acids and sarcosine (amino acid). Sarcosine is the N-methyl derivative of glycine. Sarcosine is a natural amino acid found in muscles and other tissues. Sarcosine is found naturally as an intermediate in the metabolism of choline to glycine. In a preferred embodiment, the sarcosines are acyl sarcosines. Examples of acyl sarcosines include, but are not limited to, cocoyl sarcosine, lauroyl sarcosine, myristoyl sarcosine, oleoyl sarcosine, stearoyl sarcosine which are modified fatty acids. The salts of acyl sarcosines are referred to acyl sarcosinates. Acyl sarcosinates useful herein include, for example, those having a formula:

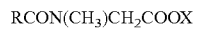

wherein R is an alkyl or alkenyl having from 8 to 22 carbon atoms, preferably from 12 to 18 carbon atoms, more preferably from 12 to 14 carbon atoms; and X is a sodium, potassium, ammonium, or triethanolamine.

Examples of acyl sarcosinates mat can be used with the present invention include, but are not limited to, sodium cocyl sarcosinate, sodium lauroyl sarcosinate and sodium myristoyl sarcosinate, sodium oleoyl sarcosinate, sodium stearoyl sarcosinate, ammonium coccyl sarcosinate, ammonium lauroyl sarcosinate and ammonium myristoyl sarcosinate, ammonium oleoyl sarcosinate and ammonium stearoyl sarcosinate. Commercially available preferred acyl sarcosinates include, but are not limited to, for example, sodium lauroyl sarcosinate having the tradename HAMPOSYL L30 which is available from Hampshire Chemicals, and sodium cocoyl sarcosinate having the tradename HAMPOSYL C30 which is also available from Hampshire Chemicals.

Other suitable surfactants include fatty alcohol sulfates which have a higher alcohol or alkyl group normally in the range of 10 to 18 carbon atoms. The cation will almost invariably be sodium or will include sodium, although other cations, such as triethanolamine, potassium, ammonium, magnesium or calcium may also be used. Preferred fatty alcohol sulfates are those wherein the fatty alcohol is essentially saturated and is of a carbon content(s) within the 10 to 18 carbon atoms range, preferably 10 or 12 to 14 or 16 carbon atoms, such as 12 to 16, or that is derived from coconut oil (coco), palm oil, or palm kernel oil. Lauryl sulfates, and particularly, sodium lauryl sulfate, are preferred primary detergents but such designation also may apply to such detergents wherein the carbon chain length of the alcohol is not limited to 12 carbon atoms, but is primarily (over 50% and normally over 70 or 75%) of 12 to 14 carbon atoms. Such materials may be obtained from natural sources, such as coconut oil and palm kernel oil. In one embodiment, the fatty alcohol sulfate is a $C_{12}$-$C_{18}$ fatty alcohol sulfate. In another embodiment, the fatty alcohol sulfate is a $C_{12}$-$C_{16}$ fatty alcohol sulfate. In another embodiment, the fatty alcohol sulfate is a $C_{12}$-$C_{14}$ fatty alcohol sulfate. In another embodiment, the fatty alcohol is a $C_{12}$ fatty alcohol sulfate. In another embodiment, the fatty alcohol sulfate is sodium lauryl sulfate. In a specific embodiment, the fatty alcohol sulfate is a sodium coco fatty alcohol sulfate.

Suitable amphoteric surfactants for use herein include the amine oxide surfactants and the alkyl amphocarboxylic acids. Suitable amine oxides include those compounds having the formula R$_3$(OR$^4$)$_x$NO(R$^5$)$_2$ wherein R$^3$ is selected from an alkyl, hydroxyalkyl, acylamidopropyl and alkylphenyl group, or mixtures thereof containing from 8 to 26 carbon atoms; R$^4$ is an alkylene or hydroxyalkylene group containing from 2 to 3 carbon atoms, or mixtures thereof, x is from 0 to 5, preferably from 0 to 3; and each R$^5$ is an alkyl or hydroxyalkyl group containing from 1 to 3, or a polyethylene oxide group containing from 1 to 3 ethylene oxide groups. Suitable amine oxides are $C_{10}$-$C_{18}$ alkyl dimethylamine oxide, and $C_{10}$-$C_{18}$ acylamido alkyl dimethylamine oxide. A suitable example of an alkyl amphodicarboxylic acid is MIRANOL C2M Conc. manufactured by Miranol, Inc., Dayton, N.J.

Zwitterionic surfactants may also be incorporated into the cleaning compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine suitable surfactants are exemplary zwitterionic surfactants for use herein.

Suitable betaines are those compounds having the formula $R(R^1)_2N^+R^2COO^-$ wherein R is a $C_6$-$C_{18}$ hydrocarbyl group, each $R^1$ is typically $C_1$-$C_3$ alkyl, and $R^2$ is a $C_1$-$C_5$ hydrocarbyl group. Suitable betaines are $C_{12}$-$C_{18}$ dimethyl-ammonio hexanoate and the $C_{10}$-$C_{18}$ acylamidopropane (or ethane) dimethyl (or diethyl) betaines. Complex betaine surfactants are also suitable for use herein.

Suitable cationic surfactants to be used herein include the quaternary ammonium surfactants. The quaternary ammonium surfactant may be a mono $C_6$-$C_{16}$, or a $C_6$-$C_{10}$ N-alkyl or alkenyl ammonium surfactant wherein the remaining N positions are substituted by methyl, hydroxyethyl or hydroxypropyl groups. Suitable are also the mono-alkoxylated and bis-alkoxylated amine surfactants. Additional suitable cationic surfactants include coco fatty acid diethanolamine, hydrogenated palm tea ester quat, and cationic ethyoxylate fatty acids.

Another suitable group of cationic surfactants, which can be used in the cleaning compositions, are cationic ester surfactants. The cationic ester surfactant is a compound having surfactant properties comprising at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529, each of which is herein incorporated by reference. The ester linkage and cationically charged group may be separated from each other in the surfactant molecule by a spacer group consisting of a chain comprising at least three atoms (i.e. of three atoms chain length), or from three to eight atoms, or from three to five atoms, or three atoms. The atoms forming the spacer group chain are selected from the group consisting of carbon, nitrogen, and oxygen atoms and any mixtures thereof, with the proviso that any nitrogen or oxygen atom in said chain connects only with carbon atoms in the chain. Thus spacer groups having, for example, —O—O— (i.e. peroxide), and —N—N—, and —N—O— linkages are excluded, whilst spacer groups having, for example —CH$_2$—O—, CH$_2$— and —CH$_2$—NH—CH$_2$— linkages are included. The spacer group chain may comprise only carbon atoms, or the chain may be a hydrocarbyl chain.

The cleaning composition may comprise cationic mono-alkoxylated amine surfactants, for instance, of the general formula: $R^1R^2R^3N^+A_pR^4X^-$ wherein $R^1$ is an alkyl or alkenyl moiety containing from about 6 to about 18 carbon atoms, or from 6 to about 16 carbon atoms, or from about 6 to about 14 carbon atoms; $R^2$ and $R^3$ are each independently alkyl groups containing from one to about three carbon atoms, for Instance, methyl for instance, both $R^2$ and $R^3$ are methyl groups; $R^4$ is selected from hydrogen, methyl and ethyl; $X^-$ is an anion such as chloride, bromide, methylsulfate, sulfate, or the like, to provide electrical neutrality; A is a alkoxy group, especially a ethoxy, propoxy or butoxy group; and p is from 0 to about 30, or from 2 to about 15, or from 2 to about 8. The $A_pR^4$ group in the formula may have p=1 and is a hydroxyalkyl group, having no greater than 6 carbon atoms whereby the —OH group is separated from the quaternary ammonium nitrogen atom by no more than 3 carbon atoms. Suitable $A_pR^4$ groups are —CH$_2$CH$_2$—OH, —CH$_2$CH$_2$CH$_2$—OH, —CH$_2$CH(CH$_3$)—OH and —CH(CH$_3$)CH$_2$—OH. Suitable $R^1$ groups are linear alkyl groups, for instance, linear $R^1$ groups having from 8 to 14 carbon atoms.

Suitable cationic mono-alkoxylated amine surfactants for use herein are of the formula $R^1(CH_3)(CH_3)N^+(CH_2CH_2O)_{2-5}HX^-$ wherein $R_1$ is $C_{10}$-$C_{18}$ hydrocarbyl and mixtures thereof especially $C_{10}$-$C_{14}$ alkyl or $C_{10}$ and $C_{12}$ alkyl and X is any convenient anion to provide charge balance, for instance, chloride or bromide.

As noted, compounds of the foregoing type include those wherein the ethoxy (CH$_2$CH$_2$O) units (EO) are replaced by butoxy, isopropoxy [CH(CH$_3$)CH$_2$O] and [CH$_2$CH(CH$_3$)O] units (i-Pr) or n-propoxy units (Pr), or mixtures of EO and/or Pr and/or i-Pr units.

The cationic bis-alkoxylated amine surfactant may have the general formula: $R^1R^2N^+A_pR^3A'_qR^4X^-$ wherein $R^1$ is an alkyl or alkenyl moiety containing from about 8 to about 18 carbon atoms, or from 10 to about 16 carbon atoms, or from about 10 to about 14 carbon atoms; $R^2$ is an alkyl group containing from one to three carbon atoms, for instance, methyl; $R^3$ and $R^4$ can vary independently and are selected from hydrogen, methyl and ethyl, $X^-$ is au anion such as chloride, bromide, methylsulfate, sulfate, or the like, sufficient to provide electrical neutrality. A and A' can vary independently and are each selected from $C_1$-$C_4$ alkoxy, for instance, ethoxy, (i.e., —CH$_2$CH$_2$O—), propoxy, butoxy and mixtures thereof, p is from 1 to about 30, or from 1 to about 4 and q is from 1 to about 30, or from 1 to about 4, or both p and q are 1.

Suitable cationic bis-alkoxylated amine surfactants for use herein are of the formula $R^1CH_3N^+(CH_2CH_2OH)(CH_2OH)X^-$, wherein $R^1$ is $C_{10}$-$C_{18}$ hydrocarbyl and mixtures thereof, or $C_{10}$, $C_{12}$, $C_{14}$ alkyl and mixtures thereof $X^-$ is any convenient anion to provide charge balance, for example, chloride. With reference to the general cationic bis-alkoxylated amine structure noted above, since in one example compound $R^1$ is derived from (coconut) $C_{12}$-$C_{14}$ alkyl fraction fatty acids, $R^2$ is methyl and $A_pR_3$ and $A'_qR^4$ are each monoethoxy.

Other cationic bis-alkoxylated amine surfactants useful herein include compounds of the formula: $R^1R^2N^+$—(CH$_2$CH$_2$O)$_p$H—(CH$^2$CH$^2$O)$_q$HX$^-$ wherein $R^1$ is $C_{10}$-$C_{18}$ hydrocarbyl, or $C_{10}$-$C_{14}$ alkyl, independently p is 1 to about 3 and q is 1 to about 3, $R^2$ is $C_1$-$C_3$ alkyl, for example, methyl, and $X^-$ is an anion, for example, chloride or bromide.

Other compounds of the foregoing type include those wherein the ethoxy (CH$_2$CH$_2$O) units (EO) are replaced by butoxy (Bu) isopropoxy [CH(CH$_3$)CH$_2$O] and [CH$_2$CH(CH$_3$)O] units (i-Pr) or n-propoxy units (Pr), or mixtures of EO and/or Pr and/or i-Pr units.

In one embodiment, the inventive compositions may include at least one fluorosurfactant selected from nonionic fluorosurfactants, cationic fluorosurfactants, and mixtures thereof which are soluble or dispersible in the aqueous compositions taught herein, sometimes compositions which do not include further detersive surfactants, or further organic solvents, or both. Suitable nonionic fluorosurfactant compounds are found among the materials presently commercially marketed under the tradename FLUORAD (ex. 3M Corp.) Exemplary fluorosurfactants include those sold as FLUORAD FC-740, generally described to be fluorinated alkyl esters; FLUORAD FC-430, generally described to be fluorinated alkyl esters; FLUORAD FC-431, generally described to be fluorinated alkyl esters; and, FLUORAD FC-170-C, which is generally described as being fluorinated alkyl polyoxyethlene ethanols.

An example of a suitable cationic fluorosurfactant compound has the following structure: $C_nF_{2n+1}SO_2NHC_3H_6N^+(CH_3)_3I^-$ where n is about 8. This cationic fluorosurfactant is available under the tradename FLUORAD FC-135 from 3M. Another example of a suitable cationic fluorosurfactant is F$_3$—(CF$_2$)$_2$— (CH$_2$)$_m$SCH$_2$CHOH—CH$_2$N$^+$R$^1$R$^2$R$^3$Cl$^-$ wherein: n is 5-9 and m is 2, and R$^1$, R$^2$ and R$^3$ are —CH$_3$. This cationic fluorosurfactant is available under the tradename ZONYL FSD (available from DuPont, described as 2-hydroxy-3-((gamma-omega-perfluoro-C$_{6-20}$-alkyl)thio)-N,N,N-trimethy-l-1-propyl ammonium chloride). Other cationic fluorosurfactants suitable for use in the present invention are also described in EP 866,115 to Leach and Niwata, herein incorporated by reference. The fluorosurfactant selected from the group of nonionic fluorosurfactant, cationic fluorosurfactant and mixtures thereof may be present in amounts of from 0.001 to 5% wt., preferably from 0.01 to 1% wt., and more preferably from 0.01 to 0.5% wt.

Some embodiments of the invention may comprise a nonionic surfactant. Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts.

The condensation products of aliphatic alcohols with from 1 to 25 moles of alkylene oxide, particularly ethylene oxide and/or propylene oxide, are suitable for use herein. The alkyl chain of the aliphatic alcohol can either be straight or branched, primary or secondary, and generally contains from 6 to 22 carbon atoms. Also suitable are the condensation products of alcohols having an alkyl group containing from 8 to 20 carbon atoms with from 2 to 10 moles of ethylene oxide per mole of alcohol.

Polyhydroxy fatty acid amides suitable for use herein are those having the structural formula R$^2$CONR$^1$Z wherein; R$^1$ is H, C$_1$-C$_4$ hydrocarbyl, 2-hydroxyethyl, 2-hydroxypropyl, ethoxy, propoxy, or a mixture thereof for instance, C$_1$-C$_4$ alkyl or C$_1$ or C$_2$ alkyl; and R$^2$ is a C$_5$-C$_{31}$ hydrocarbyl, for instance, straight-chain C$_5$-C$_{19}$ alkyl or alkenyl, or straight-chain C$_9$-C$_{17}$ alkyl or alkenyl, or straight-chain C$_{11}$-C$_{17}$ alkyl or alkenyl, or mixture thereof, and Z is a polyhydroxyhydrocarbyl having a linear hydrocarbyl chain with at least 3 hydroxyls is directly connected to the chain, or an alkoxylated derivative (for example, ethoxylated or propoxylated) thereof. Z may be derived from reducing a sugar in a reductive amination reaction, for example, Z is a glycityl.

Suitable fatty acid amide surfactants include those having the formula: R$^1$CON(R$^2$)$_2$ wherein R$^1$ is an alkyl group containing from 7 to 21, or from 9 to 17 carbon atoms and each R$^2$ is selected from the group consisting of hydrogen, C$_1$-C$_4$ alkyl, C$_1$-C$_4$ hydroxyalkyl, and —(C$_2$H$_4$O)$_x$H, where x is in the range of from 1 to 3.

Suitable alkylpolysaccharides for use herein are disclosed in U.S. Pat. No. 4,565,647 to Llenado, herein incorporated by reference, having a hydrophobic group containing from 6 to 30 carbon atoms and a polysaccharide, e.g., a polyglycoside, hydrophilic group containing from 1.3 to 10 saccharide units. Alkylpolyglycosides may have the formula: R$^2$O(C$_n$H$_{2n}$O)$_t$(glycosyl)$_x$ wherein R$^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl may be derived from glucose.

Other suitable nonionic surfactants are food safe nonionic surfactants. Examples of food safe nonionic surfactants are sucrose esters, such as sucrose cocoate available from Croda, and sorbitan esters, such as polyoxyethylene (20) sorbitan monooleate from J. T. Baker and polyoxyethylene (20) sorbitan monolaurate from Uniquema. Other examples of food safe nonionic surfactants are given in Generally Recognized As Safe (GRAS) lists, as described below.

In one embodiment, the compositions may specifically contain alkyl polyglucoside ("APG") surfactant. Suitable alkyl polyglucoside surfactants are the alkylpolysaccharides that are disclosed in U.S. Pat. No. 5,776,872 to Giret et al.; U.S. Pat. No. 5,883,059 to Furman et al.; U.S. Pat. No. 5,883, 062 to Addison et al.; and U.S. Pat. No. 5,906,973 to Ouzounis et al. which are all incorporated by reference. Suitable alkyl polyglucosides for use herein are also disclosed in U.S. Pat. No. 4,565,647 to Llenado (also incorporated by reference) describing alkylpolyglucosides having a hydrophobic group containing from about 6 to about 30 carbon atoms, or from about 10 to about 16 carbon atoms and polysaccharide, e.g., a polyglycoside, hydrophilic group containing from about 1.3 to about 10, or from about 1.3 to about 3, or from about 1.3 to about 2.7 saccharide units. Optionally, there can be a polyalkyleneoxide chain joining the hydrophobic moiety and the polysaccharide moiety. A suitable alkyleneoxide is ethylene oxide. Typical hydrophobic groups include alkyl groups, either saturated or unsaturated, branched or unbranched containing from about 8 to about 18, or from about 10 to about 16 carbon atoms. The alkyl group may contain up to about 3 hydroxy groups and/or the polyalkyleneoxide chain cart contain up to about 10, or less than about 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

Suitable alkylpolyglycosides (or alkylpolyglucosides) have the formula: R$^2$O(C$_n$H$_{2n}$O)$_t$(glucosyl)$_x$ wherein R$^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14 carbon atoms; n is about 2 or about 3, preferably about 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glycoside (attachment at the 1-position). The additional glycosyl units can then be attached between their 1-position and the preceding glycosyl units 2-, 3-, 4- and/or 6-position, preferably predominantly the 2-position.

A group of alkyl glycoside surfactants suitable for use in the practice of this invention may be represented by formula I below:

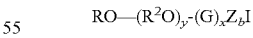

wherein R is a monovalent organic radical containing from about 6 to about 30 (preferably from about 8 to about 18) carbon atoms; R$_2$ is a divalent hydrocarbon radical containing from about 2 to about 4 carbon atoms; O is an oxygen atom; y is a number which has an average value from about 0 to about 1 and is preferably 0; G is a moiety derived from reducing a saccharide containing 5 or 6 carbon atoms; and x is a number having an average value from about 1 to 5 (preferably from 1.1 to 2); Z is O$_2$M$^1$, O$_2$CR$^3$, O(CH$_2$), CO$_2$M$^1$, OSO$_3$M$^1$, or O(CH$_2$)SO$_3$M$^1$; R$^3$ is (CH$_2$)CO$_2$M$^1$ or CH=CHCO$_2$M$^1$; (with the proviso that Z can be O$_2$M$^1$ only if Z is in place of a primary hydroxyl group in which the primary hydroxyl-bearing carbon atom, —CH$_2$OH, is oxidized to form a—CO$_2$M$^1$ group; b is a number from 0 to 3x+1 preferably an average of from 0.5 to 2 per glycosal group; p is 1 to 10, M$^1$ is H$^+$ or an organic or inorganic cation, such as, for example, an alkali metal, ammonium, monoethanolamine, or calcium. As defined in Formula I, R is generally the residue of a fatty alcohol having from about 8 to 30 or 8 to 18 carbon atoms. Suitable alkylglycosides include, for example, APG 325 (a C$_9$-C$_{11}$ alkyl polyglycoside available from Cognis Corporation), APG 625 (a C$_{10}$-C$_{16}$ alkyl polyglycoside available from Cognis Corporation), Dow TRITON CG110 (a C$_8$-C$_{10}$ alkyl polyglycoside available from Dow Chemical Company), AG6202 (a C$_8$ alkyl polyglycoside available from Akzo Nobel) GLUCOPON 425N (a C$_8$-C$_{16}$ alkyl polyglycoside available from Cognis Corporation), GLUCOPON 215 (a C$_8$-C$_{10}$ alkyl polyglycoside available from Cognis Corporation), GLUCOPON 225 (a C$_8$-C$_{10}$ alkyl polyglycoside available from Cognis Corporation) and ALKADET 150 (a C$_8$-C$_{10}$ alkyl polyglycoside available from Huntsman Corporation). A C$_8$ to C$_{10}$ alkylpoly-glucoside includes alkylpolyglucosides wherein the alkyl group is substantially C$_8$ alkyl, substantially C$_{10}$ alkyl, or a mixture of substantially C$_8$ and C$_{10}$ alkyl. Additionally, short chain APGs such as C$_4$ and/or C$_6$ or mixtures thereof may be suitable for use with the present invention.

In one embodiment, the composition contains no enzymes, waxes, resins, nonionic surfactants, chlorite salts, or chloride dioxide.

IX. Hydrotropes

The composition may include one or more hydrotropes for solubilizing the other components of the composition upon addition of water. The hydrotrope solubilizing materials, when used, include, but are not limited to water soluble salts of low molecular weight organic acids such as the alkali metal (sodium and/or potassium) salts of aromatic sulfonic acids. Specific exemplary materials include, but are not limited to, toluene sulfonate, cumene sulfonate, xylene sulfonate, naphthalene sulfonate, methyl naphthalene sulfonate, and combinations thereof.

The hydrotropes may be present at a level of from about 0.1% to about 25%, from about 0.1% to about 20%, from about 0.1% to about 15%, from about 0.1% to about 10%, from about 0.1% to about 5%.

X. Additional Adjuncts

In some embodiments, the compositions may optionally contain one or more of the following adjuncts: colorants, perfumes, sequestrants, anti-corrosion agents, lubricants, binders, fillers, disintegration aids, preservatives, or desiccants. Other adjuncts include, but are not limited to, acids, electrolytes, stabilizers, thickeners, defoamers, cloud point modifiers, stain and soil repellants, odor control agents, brighteners, fluorescent whitening agents, and solid processing aids. Binders, when used, include, but are not limited to, celluloses, starches, gums, and synthetic polymers. Solid processing aids, when used, include, but are not limited to, flow aids, lubricants, anti-static agents, and glidants. Electrolytes, when used, may include, but are not limited to, calcium, sodium and potassium chloride. Thickeners, when used, include, but are not limited to, xanthan gum, calcium carbonate, cellulose, aluminum oxide, alginates, guar gum, methyl ethyl clays, and/or propyl hydroxycelluloses. Defoamers, when used, include, but are not limited to, silicones, aminosilicones, silicone blends, and/or silicone/hydrocarbon blends.

Preservatives, when used, include, but are not limited to, mildewstat or bacteriostat, methyl ethyl and propyl parabens, phosphates such as trisodium phosphate, short chain organic acids (e.g. acetic, lactic and/or glycolic acids), bisguanidine compounds (e.g. DANTAGARD and/or GLYDANT) and/or short chain alcohols (e.g. ethanol and/or isopropyl alcohol). The mildewstat or bacteriostat includes, but is not limited to, mildewstats (including non-isothiazolone compounds) including KATHON GC, a 5-chloro-2-methyl-4-isothiazolin-3-one, KATHON ICP, a 2-methyl-isothiazolin-3-one, and a blend thereon and KATHON 886, 5-chloro-2-methyl-4-isothiazolin-3-one, all available from Rohm and Haas Company; BRONOPOL, a 2-bromo-2-nitropropane 1,3 diol, from Boots Company Ltd., PROXEL CRL, a propyl-p-hydroxybenzoate, from ICI PLC; NIPASOL M, an o-phenyl-phenol, Na$^+$ salt, from Nipa Laboratories Ltd., DOWICIDE A, a 1,2-Benzoisothiazolin-3-one, from Dow Chemical Co., Nipacides from Clariant, and IRGASAN DP 200, a 2,4,4'-trichloro-2-hydroxydiphenylether, from Ciba-Geigy A.G.

XI. Forms and Uses

The compositions of the present invention may be used in the disinfection of dentures, although other uses of the composition (e.g., as a mouthwash, or for endodontic root canal disinfection) are also contemplated. The one-layered composition of the present invention is preferably in the form of a single-layer substantially homogenous tablet, although it may alternatively take the form of a powder or granules. The present invention is directed to composition claims and methods of using the composition. Generally, methods steps of using the composition include contacting a specific surface (e.g., dentures) with the composition in water so as to clean the specific surface with the composition.

XII. Examples

Without limitation, the following examples illustrate exemplary implementation of the present invention:

TABLE 1

| | Example Compositions 1-4 | | | |
|---|---|---|---|---|
| Ingredient | Example 1 Wt. % active | Example 2 Wt. % active | Example 3 Wt. % active | Example 4 Wt. % active |
| Calcium hypochlorite | 1.65 | 4.75 | 1.65 | 0.34 |
| Succinic acid | 56.64 | 54.37 | 56.64 | 57.60 |
| Sodium carbonate | 36.28 | 34.83 | 36.28 | 36.90 |
| Maleic acid/acrylic acid copolymer | 2.09 | 2.01 | 2.09 | 2.13 |
| Sodium carboxymethyl cellulose | 0.11 | 0.11 | 0.11 | 0.11 |

TABLE 1-continued

Example Compositions 1-4

| Ingredient | Example 1 Wt. % active | Example 2 Wt. % active | Example 3 Wt. % active | Example 4 Wt. % active |
|---|---|---|---|---|
| Sodium xylene sulfonate | 1.39 | 1.34 | 1.39 | 1.42 |
| Sodium lauryl sulfonate | 1.39 | | | |
| Sodium linear alkylbenzene sulfonate | | 1.34 | 1.39 | 1.42 |
| Weight per use, g | 2.726 | 2.840 | 2.726 | 2.680 |
| HOCl, ppm when dissolved in 150 mL of water | 211 | 634 | 211 | 42 |

The compositions in Table 1 were initially prepared as powders. The powders in the above table were prepared and dissolved in 150 mL of water to make a cleaning solution for dentures and dental appliances. All of the powders displayed effervescence and created foam to signal cleaning power. They also released the indicated amount of hypochlorous acid to disinfect and remove stains, plaque and biofilms. The pH of the cleaning solution was between pH 5.5 and pH 6.5.

Each of the powders in Table 1 were compressed into single-layer tablets to deliver the desired weight per use. All the tablets dissolved within 5 minutes with effervescence and foam. They all released the targeted concentration of hypochlorous acid when added to 150 mL of water and had a pH between 5.5 and 6.5.

Additional exemplary compositions 5-19 are described in Tables 2-4, below.

TABLE 2

Example Compositions 5-9

| Ingredient | Example 5 Wt. % active | Example 6 Wt. % active | Example 7 Wt. % active | Example 8 Wt. % active | Example 9 Wt. % active |
|---|---|---|---|---|---|
| Calcium hypochlorite, 79% wt | 49.88 | 32.34 | 2.11 | 1.03 | 0.87 |
| Sodium polyacrylate (MW = 5,100) | | 2.43 | | | |
| adipic acid | 31.42 | | | 53.20 | 41.52 |
| Sodium polyacrylate (MW = 2800) | 0.95 | | | | |
| Sodium polyacrylate; maleic copolymer (MW = 4,500) | | | 2.11 | | 1.97 |
| Sodium polyacrylate; maleic copolymer (MW = 2,800) | | | | 1.96 | |
| Hydroxypropyl cellulose | 0.05 | | | | |
| Microcrystalline cellulose | | | | 0.10 | |
| Sodium linear alkylbenzene sulfonate | | 5.78 | 1.41 | 1.31 | |
| Sodium xylene sulfonate | 0.63 | 0.88 | 0.36 | 0.34 | 1.31 |
| Polyvinylpyrrolidone (PVP) grade K-13/19 | | | 0.19 | | |
| Sodium carbonate | 16.44 | 22.85 | 36.63 | | 34.22 |
| Sodium carboxmethyl cellulose | | 0.07 | | | 0.10 |
| Sodium sesquicarbonate | | | | 42.06 | |
| Sodium lauryl sulfate | 0.63 | | | | 1.32 |
| Succinic acid | | 35.65 | 57.19 | | 18.69 |
| Weight per use, g | 6.02 | 4.33 | 2.70 | 2.90 | 2.89 |
| HOCl, ppm when dissolved in 150 mL of water | 11147 | 5259 | 216 | 114 | 95 |

TABLE 3

Example Compositions 10-14

| Ingredient | Example 10 Wt. % active | Example 11 Wt. % active | Example 12 Wt. % active | Example 13 Wt. % active | Example 14 Wt. % active |
|---|---|---|---|---|---|
| Calcium hypochlorite, 79% wt | 8.78 | 0.52 | 2.99 | 8.56 | 0.26 |
| 3-pyridinesulfonic acid | | | 46.23 | | |
| sodium polyacrylate (MW = 5,100) | | | | 1.95 | |
| Adipic acid | | | | | 39.56 |
| Sodium polyacrylate (MW = 2800) | | 1.48 | 1.71 | | |
| Alkyldiphenyloxide disulfonate | | | | 1.30 | 5.12 |

TABLE 3-continued

Example Compositions 10-14

| Ingredient | Example 10 Wt. % active | Example 11 Wt. % active | Example 12 Wt. % active | Example 13 Wt. % active | Example 14 Wt. % active |
|---|---|---|---|---|---|
| Alkylnaphthalene sulfonate | | | | | 2.56 |
| Sodium polyacrylate, maleic copolymer (MW = 4,500) | | | | | 1.46 |
| Crosslinked sodium carboxymethylcellulose | 0.07 | | | | |
| Glutaric acid | | | | 52.89 | |
| Hydroxypropyl cellulose | | | | | 0.08 |
| Linear alkyl benzene sulfonic acid | | 31.21 | | | |
| Sodium linear alkylbenzene sulfonate | | | 1.14 | | |
| Sodium xylene sulfonate | 0.83 | 0.99 | | | |
| Polyacrylic acid (MW <= 6000) | 33.89 | | | | |
| Polyvinylpyrrolidone (PVP) grade K-13/19 | | | | 0.10 | |
| Sodium bicarbonate | | | 46.70 | | |
| Sodium bisulfate | | | | | 12.81 |
| Sodium carbonate | 21.71 | 25.72 | | 33.90 | 25.34 |
| Sodium carboxymethyl cellulose | | 0.08 | 0.09 | | |
| Sodium sulfate | 33.89 | 39.01 | | | |
| Sodium xylene sulfonate | | | | 1.30 | |
| Sodium lauryl sulfate | 0.83 | 0.99 | 1.14 | | |
| Succinic acid | | | | | 12.81 |
| Weight per use, g | 4.56 | 3.85 | 3.34 | 2.92 | 3.90 |
| HOCl, ppm when dissolved in 150 mL of water | 1500 | 75 | 378 | 948 | 38 |

TABLE 4

Example Compositions 15-19

| Ingredient | Example 15 Wt. % active | Example 16 Wt. % active | Example 17 Wt. % active | Example 18 Wt. % active | Example 19 Wt. % active |
|---|---|---|---|---|---|
| Magnesium hypochlorite, 52% wt | 49.88 | 1.53 | 1.29 | 22.79 | 0.74 |
| Calcium hypochlorite, 79% wt | | | 25.73 | 1.14 | 0.74 |
| Adipic acid | 31.42 | 57.67 | 25.73 | 22.79 | 29.52 |
| Alkyl diphenyloxide disulfonate | | | 0.96 | 0.87 | 1.12 |
| Alkylnapthalene sulfonate | | | 1.29 | 1.14 | 1.48 |
| Crosslinked sodium carboxylmethyl cellulose | | 0.09 | | | |
| Hydroxypropyl cellulose | 0.05 | | | | |
| Microcrystalline cellulose | | | | 0.07 | 0.09 |
| Polyvinylpyrrolidone (PVP) grade K-13/19 | | | 0.08 | | |
| Sodium bisulfate | | | 10.29 | 9.12 | 11.81 |
| Sodium carbonate | 16.44 | 30.18 | 25.44 | 22.54 | 29.20 |
| Sodium lauryl sulfate | | 1.16 | | | |
| Sodium linear alkylbenzene sulfonate | 0.63 | | | | |
| Sodium polyacrylate (MW = 2800) | 0.95 | | 1.47 | 1.30 | 1.68 |
| Sodium polyacrylate (MW = 5,100) | | 1.74 | | | |
| Sodium sesquicarbonate | | | | 11.40 | 14.76 |
| Sodium xylene sulfonate | 0.63 | 1.53 | | | |
| Succinic acid | | 6.10 | 7.72 | 6.84 | 8.86 |
| Weight per use, g | 6.02 | 3.28 | 3.89 | 4.39 | 3.39 |
| HOCl, ppm when dissolved in 150 mL of water | 8248 | 140 | 3906 | 2966 | 164 |

We claim:

1. A solid, one-layered composition comprising:
   i. a hypochlorite selected from the group consisting of calcium hypochlorite, magnesium hypochlorite and mixtures thereof;
   ii. a builder selected from the group consisting of carbonate, bicarbonate, sesquicarbonate and mixtures thereof;
   iii. at least 30% by weight of an acid selected from the group consisting of a carboxylic acid, a dicarboxylic acid, a sulfonic acid, an acid sulfate, an acid phosphate, and mixtures thereof;
   iv. a water-soluble polymer selected from the group consisting of a polycarboxylate, a sulfonated carboxylate, a polysulfonate, a polyvinylpyrrolidone, a polypyridinium salt, a polyquaternary ammonium salt, and mixtures thereof; and
   wherein the composition does not contain potassium hypochlorite, sodium hypochlorite, lithium hypochlorite, N-halogenated compounds, peroxides, persulfates, hydantoins, isocyanurates, carboxylic acids that also have hydroxyl, amino, amido, imino, or imido groups;
   wherein the composition contains only one layer.

2. The composition of claim 1, wherein the hypochlorite is the calcium hypochlorite and the calcium hypochlorite comprises less than 50% by weight of the composition.

3. The composition of claim 1, wherein the acid comprises at least 50% by weight of the composition.

4. The composition of claim 1, wherein the acid is the dicarboxylic acid.

5. The composition of claim 1, wherein the water-soluble polymer is the polycarboxylate, and where the carboxylate ions for the polycarboxylate are derived from the group consisting of maleic acid, acrylic acid, methacrylic acid and mixtures thereof.

6. The composition of claim 1, further comprising at least one hydrotrope.

7. The composition of claim 6, wherein the hydrotrope is a salt selected from the group consisting of a toluene sulfonate, a cumene sulfonate, a xylene sulfonate, a naphthalene sulfonate, a methyl naphthalene sulfonate, and mixtures thereof.

8. The composition of claim 7, wherein the composition does not contain enzymes, waxes, resins, nonionic surfactants, chlorite salts, or chlorine dioxide.

9. The composition of claim 1, further comprising at least one anionic surfactant.

10. A solid, one-layered composition consisting essentially of:
    i. a hypochlorite selected from the group consisting of calcium hypochlorite, magnesium hypochlorite and mixtures thereof;
    ii. a builder selected from the group consisting of carbonate, bicarbonate, sesquicarbonate and mixtures thereof;
    iii. at least 30% by weight of an acid selected from the group consisting of a carboxylic acid, a dicarboxylic acid, a sulfonic acid, an acid sulfate, an acid phosphate, and mixtures thereof;
    iv. a water-soluble polymer selected from the group consisting of a polycarboxylate, a sulfonated carboxylate, a polysulfonate, a polyvinylpyrrolidone, a polypyridinium salt, a polyquaternary ammonium salt, and mixtures thereof;
    v. at least one hydrotrope; and
    vi. optionally, a cobuilder selected from the group consisting of a hydroxide, an oxide, a silicate, a phosphate, a borate and mixtures thereof; and
    vii. optionally, colorants, perfumes, sequestrants, anti-corrosion agents, lubricants, binders, fillers, disintegration aids, preservatives, desiccants, and mixtures thereof.

11. The composition of claim 10, wherein the composition does not comprise any potassium hypochlorite, sodium hypochlorite, lithium hypochlorite, N-halogenated compounds, peroxides, persulfates, hydantoins, isocyanurates, carboxylic acids that have hydroxyl, amino, amido, imino, or imido group, enzymes, waxes, resins, or nonionic surfactants.

12. The composition of claim 10, wherein the hypochlorite is calcium hypochlorite and the calcium hypochlorite comprises less than 50% by weight of the composition.

13. The composition of claim 10, further comprising at least one anionic surfactant.

14. The composition of claim 10, wherein the acid is a dicarboxylic acid.

15. The composition of claim 10, wherein the water-soluble polymer is a polycarboxylate, and where the carboxylate ions for the polycarboxylate are derived from the group consisting of maleic acid, acrylic acid, methacrylic acid and mixtures thereof.

16. The composition of claim 10, wherein the hydrotrope is a salt selected from the group consisting of a toluene sulfonate, a cumene sulfonate, a xylene sulfonate, a naphthalene sulfonate, methyl naphthalene sulfonate, and mixtures thereof.

* * * * *